United States Patent [19]

Kumabe et al.

[11] Patent Number: 4,608,019
[45] Date of Patent: Aug. 26, 1986

[54] TOOL FOR EXODONTIA

[75] Inventors: Junichiro Kumabe, Tokyo; Masaru Kumabe, 1-1, Ise 4-Chome, Kofu-shi, Yamanashi 400, both of Japan

[73] Assignee: Masaru Kumabe, Yamanashi, Japan

[21] Appl. No.: 573,911

[22] PCT Filed: May 26, 1983

[86] PCT No.: PCT/JP83/00161
§ 371 Date: Jan. 16, 1984
§ 102(e) Date: Jan. 16, 1984

[87] PCT Pub. No.: WO83/04175
PCT Pub. Date: Dec. 8, 1983

[30] Foreign Application Priority Data

May 27, 1982 [JP] Japan .................. 57-88917

[51] Int. Cl.⁴ .................. A61C 1/07; A61C 3/08
[52] U.S. Cl. .................. 433/118; 433/119; 433/124; 433/215
[58] Field of Search .................. 433/86, 118, 119, 124, 433/144, 123, 122, 215

[56] References Cited

U.S. PATENT DOCUMENTS

| 2,183,690 | 12/1939 | Ostrom | 433/122 |
| 3,086,288 | 4/1963 | Balamuth | 433/119 |
| 3,332,149 | 7/1967 | Mumaw | 433/119 |
| 4,219,619 | 8/1980 | Zarow | 433/118 |

Primary Examiner—John J. Wilson
Attorney, Agent, or Firm—Robert E. Burns; Emmanuel J. Lobato; Bruce L. Adams

[57] ABSTRACT

A dental tool is provided for extracting a tooth which is secured to an alveolar bone through a pericementum. The tool includes an elongate, flat and thin blade operatively connected to an acoustic transducer which produces ultrasonic vibrational energy. The blade has a thickness on the order of about 0.2 to 0.5 mm which is substantially less than the thickness of the pericementum to enable the blade to and cut through the pericementum located between the tooth and the alveolar bone along the profile of the tooth under excitation by the acoustic transducer. The blade transmits ultrasonic oscillation to the tooth so as to insensitize the pain transmitting system of the tooth. The pericementum is effectively cut with a reduced average cutting resistance while the insensitization is maintained.

6 Claims, 5 Drawing Figures

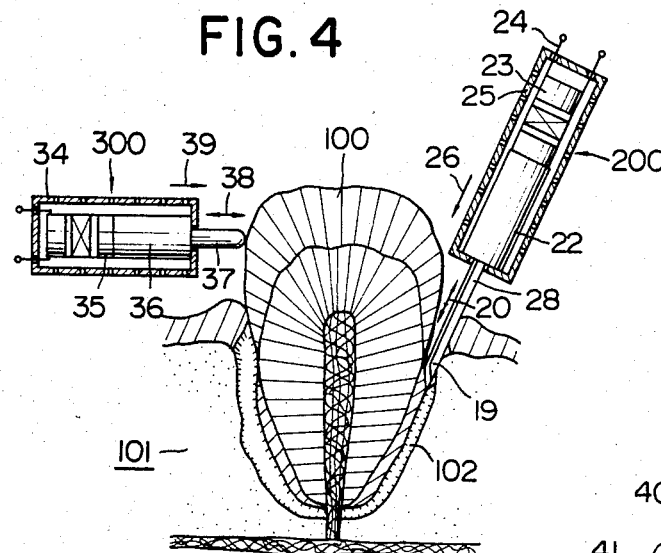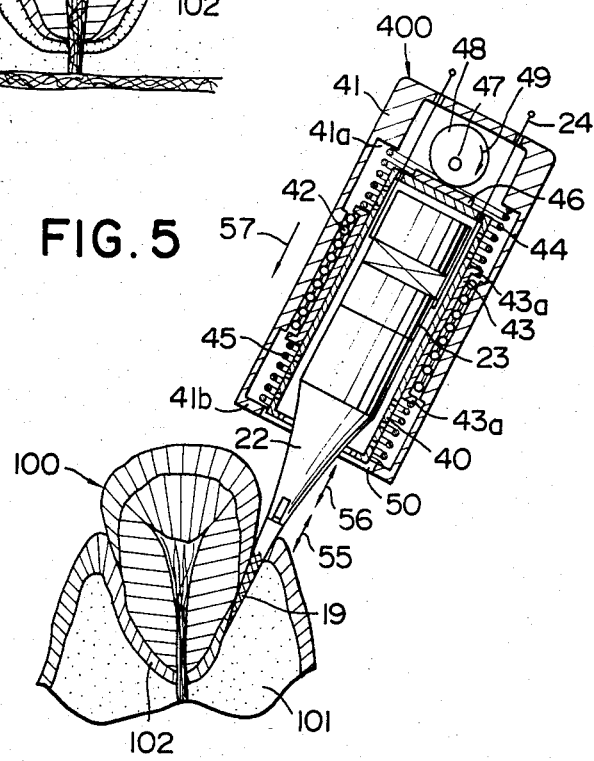

TOOL FOR EXODONTIA

FIELD OF THE INVENTION

The invention relates to a dental tool, and more particularly, to a tool for exodontia having a vibrating blade which cuts a pericementum which supports a tooth.

BACKGROUND OF THE INVENTION

The current level of exodontia still depends on a rather primitive technique, requiring a dental elevator, a rigid tool having a thickness which is substantially greater than the thickness of a pericementum and which is pierced into the pericementum which exists between a tooth and an alveolar bone which effects a wedging action and and a leverage to dig the tooth out, thus separating the pericementum of that tooth from the alveolodental wall. Subsequently, the affected tooth is extracted by means of forceps. With such exodontology, a patient cannot bear the accompanying pain without benefit of anesthesia. The current practice of exodontia with the aid of injecting narcotic causes, in addition to creating fear in the mind of the patient concerning the injection and the pain which might be experienced during the injection, a hazard of producing medicine shocks and sequelae. When narcotic is injected, also presents a patient does not experience any pain during the operation, giving rise to the tendency that a dentist may use an external force of greater magnitude than necessary in order to extract an affected tooth. This extensively destroys the alveolodental wall or the tissues of gingiva, so whereby that the patient will suffer from inflammation after the surgical operation or suffer from sequelae that unmatured permanent teeth may be damaged. It will be therefore seen that the problems found in the art of exodontia are to enable the extraction of a tooth or teeth with little or no pain while avoiding the injection of narcotic and to minimize the destruction of the alveodental walls or tissues of gingiva.

Considering a system through which pains are transmitted during a dental operation, such system can be modelled as illustrated in FIG. 1. Specifically, a tooth 100 is covered by a cement 4 and an enamel body 11, and is secured to an alveolar bone 1 through a spring 2 having a spring constant k and a dashpot 3, both of which represent the pericementum. Dentin 5 is housed within the cement 4, and interposed between the enamel body 11 and the dentin 5 are Tomes' fibers 9 and dentinal cells/fiber cells 8, carried by tooth fluid 10 within dentinal tubules and which are supported by a group of nerve fibers of the dental pulp through another spring 6 having a spring constant K and another dashpot 7 having a viscous attenuation coefficient C. Accordingly, when the Tomes' fibers 9 and dentinal cells/fiber cells 8 are subject to a static or dynamic displacement, a strain is produced in the spring 6 of the nerve fibers of the dental pulp. The magnitude of the strain can be measured by a receiver 13 of the nerve system, which corresponds to a strain gauge. The strain can be amplified by an amplifier 15 having a certain frequency response and then recorded on a recording paper 17 associated with a recorder 16 including a pen 18. It is considered that the height of the resulting waveform is proportional to the degree of pains suffered in the dental pulp. On the other hand, a displacement of the spring 2 can be measured by a strain gauge 21 which corresponds to a group of nerves distributed in the pericementum. The magnitude of such strain may be amplified by an amplifier 14 having a certain frequency response and then recorded on the recording paper 17 by the pen 18 of the recorder 16. It is considered that the height of the resulting waveform is proportional to the degree of pains suffered by the group of nerves in the pericementum. It will be seen that this model of pain transmitting system includes a pair of channels, namely, a channel leading to the dental pulp and another leading to the group of nerves in the pericementum. The extraction of a tooth is equivalent to cutting the spring 2 which corresponds to the pericementum. In the prior art practice, the cutting operation produced large strains in the spring 6 associated with the dental pulp as well as in the spring 2 associated with the pericementum, and pains from the both channels are fed to the nerve center. However, considering the nature of resistance encountered during the exodontia, it is found that such resistance is largely due to the strength of the spring 2 associated with the pericementum, and that the influence of the strength of the spring 6 associated with the dental pulp can be neglected. Accordingly, it follows that a tooth can be easily extracted by carefully cutting the pericementum which is distributed around that tooth. The spring 2 associated with the pericementum will undergo an expansion and shrinkage in proportion to the magnitude of a pressure P applied to the tooth 100 during the exodontia, and the degree of such expansion and shrinkage causes a corresponding change in the degree of pains suffered. The injection of narcotic which is used in the prior art practice in order to alleviate pains is equivalent to disconnecting the recorder 16 from the strain guage 21 associated with the spring 2 of the pericementum, thus interrupting the transmission of a signal to the recorder 16 or the nerve center. The use of a laughing gas which is sometime used in place of narcotic is equivalent to disabling the recorder 16.

SUMMARY OF THE INVENTION

It is an object of the invention to provide a tool for extracting a tooth without utilizing the injection of narcotic and while avoiding any pains that would otherwise be experienced by a patient.

It is another object of the invention to provide a tool for extracting a tooth which minimizes the destruction of the alveolodental walls or tissues of gingiva which would otherwise be caused during the exodontia.

According to the invention, there is provided a tool for extracting a tooth which is secured to an alveolar bone through pericementum, the tool comprising an acoustic tranducer for producing vibrational energy of a predetermined frequency and a predetermined amplitude, a vibrating member having its one end operatively connected to the acoustic transducer, and a blade attached to the other end of the vibrating member in a replaceable manner, the blade having a thickness which is substantially less than the thickness of the pericementum. The acoustic transducer excites the blade through the vibrating member at a vibrational frequency greater than the natural frequency of the tooth and with an amplitude at the free end of the blade which is equal to 15 micrometers at maximum or less. It is to be understood that the term "thickness of pericementum" refers to the thickness of membraniform tissues distributed between the tooth and alveolar bone, or in other words, corresponds to a distance between the tooth and the alveolar bone. Such distance slightly changes with the displacement of the tooth, but the term as used in the description of the invention refers to a distance between the tooth and the alveolodental walls in their normal condition.

In a preferred embodiment of the invention, the blade is in the form of a thin, flat plate having a width on the order of 3 to 4 mm and a thickness on the order of 0.2 to 0.5 mm. The blade is capable of ultrasonic oscillation at a frequency of 28 kHz and with an amplitude of 8 micrometers. In use, an edge of the blade is applied against the pericementum located between a tooth and an alveolodental wall and is advanced along the profile of a tooth to cut the pericementum. This causes the pain transmitting system to be disabled or insensitized by the ultrasonic oscillation of the tooth, permitting the pericementum to be cut while encountering a small resistance. As the cutting operation proceeds, the tooth tends to lift as a result of the ultrasonic oscillation exerted by the blade, whereby the cutting of the pericementum is further facilitated. This allows cutting to be advanced to the proximity of the very end of the tooth fang, and accordingly it is only necessary to pinch the tooth with a pincer to remove it.

A tooth has a low natural frequency on the order of 300 to 2,000 Hz. Accordingly, when it is brought into facial contact with a blade which oscillates at a frequency substantially higher than the natural frequency, e.g. 28 kHz, the tooth is subjected to ultrasonic oscillation at substantially the same frequency as the vibrating blade. When a detector corresponding to a strain gauge associated with the nerves is used to detect the mode of oscillation of a tooth which is subject to ultrasonic oscilation at a frequency of 28 kHz and with an amplitude of 12 micrometers and the resulting signal is fed through an amplifier, which corresponds to the perceptive nerve having a low frequency response, to a recorder which corresponds to the nerve center, it will be noted that there will be no substantial movement of a recording pen which indicates the mode of oscillation of the tooth, when considering the effect of the ultrasonic oscillation in the pain transmitting system illustrated in FIG. 1. This means that displacement of the tooth is not sensed as pain under the ultrasonic oscillation. This is simulated by an engineering arrangement in which a strain gauge is bonded to an elastic member which oscillates at a frequency within the ultrasonic range, and a change in the voltage which results from a corresponding change in the resistance of the strain gauge is fed through an amplifier for recording by a recorder. In this example, if the amplifier and/or recorder has a low frequency response, the indicated amplitude of oscillation will be less than the actual amplitude of oscillation. Such fact can be conceptualized by the fact that the absolute value of a high frequency current cannot be accurately determined by using an a.c. arnrneter usually used for 50 Hz applications. Similarly, if it is attempted to detect an ultrasonic current of 20 kHz with a galvanometer for electromagnetic oscillograph which has a low natural frequency of 500 Hz, there will be no movement of a recording pen which is proportional to the magnitude of the current. Rather, in practice, the pen will remain at the origin.

When the tooth extracting tool of the invention is used, the fact that the blade which undergoes ultrasonic oscillation has a thickness which is substantially equal to that of the pericementum or less prevents any external force of substantial magnitude from being applied to the tooth while allowing the pericementum to be cut through without substantial destruction of the alveolodental walls or tissues of gingiva. In addition, the blade causes an ultrasonic oscillation of the tooth at substantially the same frequency, thereby insensitizing the pain transmitting system. Accordingly, a patient will experience little pain during the exodontia operation even though no narcotic is injected.

BRIEF DESCRIPTION OF THE DRAWINGS

FIG. 4 is a side elevation of an auxiliary exciting tool which is preferred for use with the tool shown in FIG. 2; and FIG. 5 is a side elevation, partly in section, of a tool according to another embodiment of the invention.

DESCRIPTION OF PREFERRED EMBODIMENTS

Figure 2:
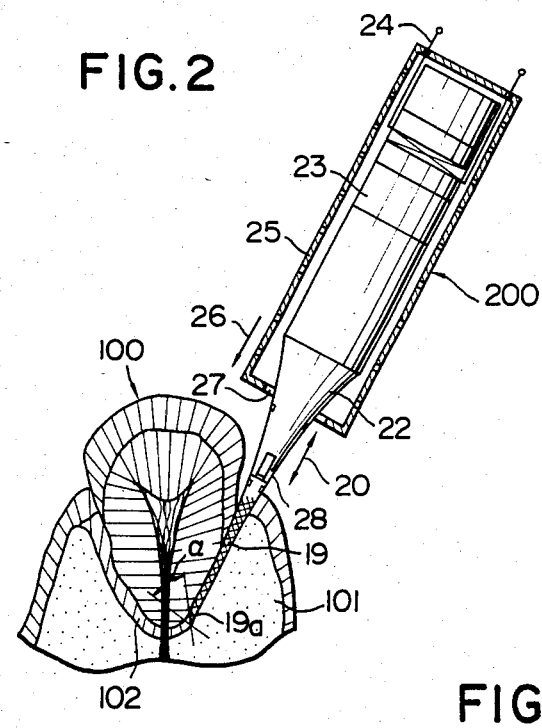
FIG. 2 is a side elevation, partly in section, of the tool of the invention.

Referring to FIG. 2, there is shown a tooth extracting tool 200 according to the invention. The tool 200 includes an ultrasonic vibrator 23 which is disposed within a cylindrical hald-held grip 25 which also serves as a housing. The vibrator 23 includes a horn 22 which operates to increase the amplitude of vibration. An end portion of the horn 22 projects through an opening 27 formed in the grip 25 and includes a terminal end 28 which carries a blade 19 in a replaceable manner. A structure for supporting the ultrasonic vibrator 23 including the horn 22 within the grip 25 is hot specifically shown, but the vibrator may be suppotted by utilizing a node of vibration of the horn 22 in a similar manner as used in various dental tools internally housing an ultrasonic vibrator such as a scaler, massager, cleaner or contra-angle, for example. Also, U.S. Pat. Nos. 3,598,012, 3,651,576, 3,924,335, 4,110,908 and 4,229,168 are cited for reference.

The blade 19 is preferably formed of stainless steel in the form of a thin flat plate having a width on the order of 3 to 4 mm, for example, and a thickness which is substantially equal to an average thickness of the pericementum or slightly less, in a range from 0.2 to 0.5 mm. Since it is formed of a very thin material, it is unnecessary to form a sharp edge on the blade 19, but it preferably is provided with a terminal end 19a having a cutting edge defined by a suitable edge angle α. The terminal end 19a may be formed as a single edge angled as shown or may have both edges. The terminal end 19a may extend along a line which is perpendicular to both lateral edges of the blade 19 or may extend on a line which is skewed thereto. It may be sometimes desirable to provide a rounded form for the terminal end 19a. However, it should be understood that such configuration is left to the choice of a dentist.

The ultrasonic vibrator 23 is connected to a pair of feed terminals 24 which are in turn connected to a source of high frequency current, not shown. When energized, the vibrator 23 oscillates, causing the horn 22 to vibrate in a longitudinal direction indicated by a double-headed arrow 20 or in the axial direction of the housing 25. The horn 22 in turn causes an ultrasonic oscillation of the blade 19 at a predetermined frequency f and with a predetermined amplitude a. The ultrasonic oscillation rigidifies the blade 19. In use, a dentist holds the grip 25 and moves the tool 200 slowly in a direction indicated by an arrow 26. Thereupon, the blade 19 bites into the pericementum 102 located between a tooth 100 and an alveolar bone 101, cutting the pericementum 102 along the profile of the tooth 100. Because the blade 19 is rigidified, there is little likelihood that a buckling of the blade 19 occurs during the cutting operation.

A length $l_T$ cut during one cycle of oscillation of the blade 19 is expressed as follows:

$$l_T = v/f$$

where v represents a feed rate and f the frequency. During the use of the tool 200 of the invention, the length $l_T$ is minimal, and since the cutting resistance is pulse-like, the average cutting resistance exhibited by the tooth 100 is minimized. Repeated experiments show that it is practical for the blade 19 to have a frequency in a range from 20 to 80 kHz and an amplitude which is equal to 15 micrometers at most or less. A greater amplitude tends to cause a reduction in the insensitizing effect of the pain transmitting system, and hence it is most desirable that an amplitude in a range from 8 to 12 micrometers be used.

While moving the tool 200 in the same direction, indicated by the arrow 26, as the direction of oscillation of the ultrasonic vibrator 23 indicated by the arrow 20, the blade 19 may be moved in a direction perpendicular to such directions or in a direction into or out of the plane of the drawing, thereby increasing the effective rake angle of the blade 19 to improve the cutting effect. This also prevents the deposition of the gingiva and blood upon the blade 19. As the cutting of the pericementum by the blade 19 proceeds to a degree, the tooth 100 becomes lifted as a result of the ultrasonic oscillation applied from the blade 19, allowing the blade 19 to cut deeper and to reach the proximity of the end of the tooth fang. During such process, a patient will experience little pain inasmuch as the pain transmitting system of the tooth 10 is insensitized by the ultrasonic oscillation. When the cutting of the pericementum proceeds to the proximity of the end of the fang, the tooth 100 can be removed, in most cases, by pinching it with a pincer.

The tool 200 of the invention has been used with the extraction of a deciduous tooth. Parameters of the blade 19 used for this operation are given below:

| | |
|---|---|
| Width: | 3 mm |
| Thickness: | 0.5 mm |
| Length: | 8 mm |
| Edge configuration: | Edges having a rake angle of 5° are formed along an end and a side with a 0.5 mm pitch saw-tooth groove in each edge |
| Frequency: | 28 kHz |
| Amplitude of vibration: | 8 micrometers |
| Output: | 40 W |

The extraction of the tooth took place without the injection of narcotic, and but the patient complained of no pain. The time required for the remedy can be reduced by one-half or one-third that of the prior practice. Since the alveolodental walls are little damaged during the exodontia, the bleeding is reduced, and thus the length of time required for recovery can be reduced by about one-half or one-tenth that of the prior practice.

Figure 1:
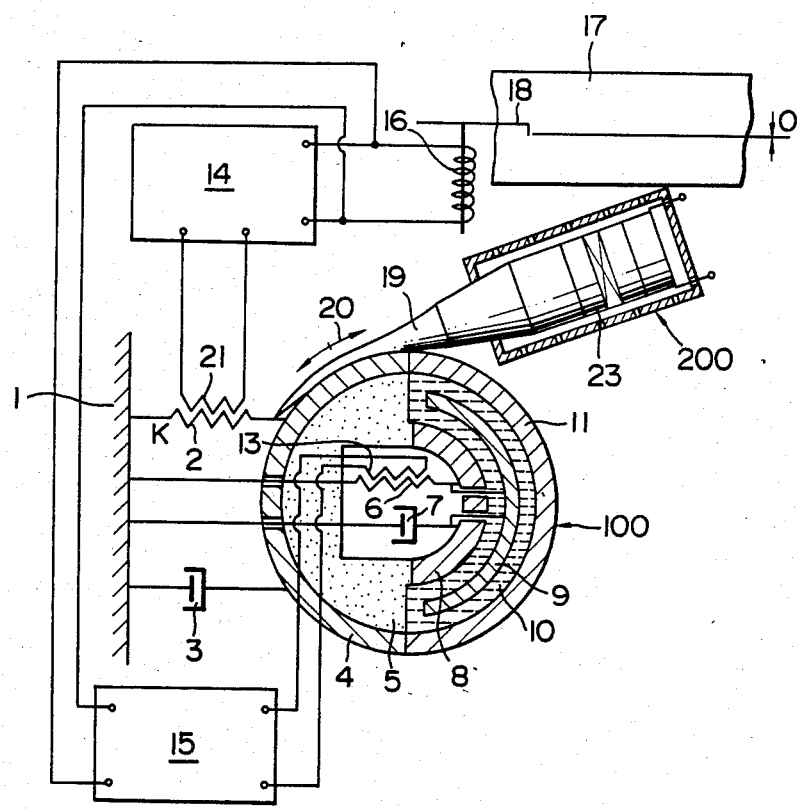
FIG. 1 is a schematic illustration of an equivalent model of a pain transmitting system of a tooth illustrating the operation of the tool according to the invention.
Figure 3:
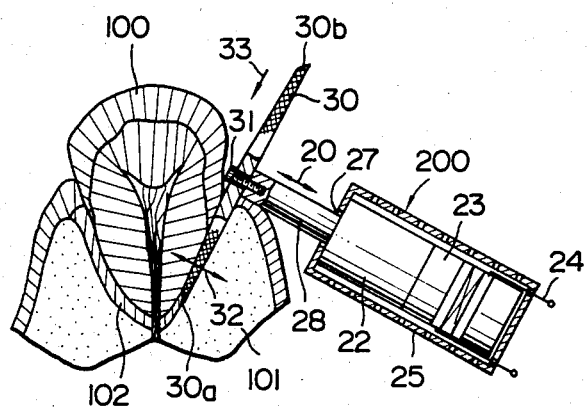
FIG. 3 is a side elevation of a modification of the tool shown in FIG. 2.

Referring to FIG. 3, there is shown a tooth extracting tool which is slightly modified from that shown in FIG. 2. In this Figure, the reference characters used in FIG. 2 are employed to designate substantially corresponding parts. An ultrasonic vibrator 23 of magnetostriction or electrostriction type is operatively connected with an amplifying horn 22 which has a different configuration from that shown in FIG. 1, but which operates in substantially the same manner. The horn 22 includes an end portion 28 which projects out of an opening 27 formed in a hand-held grip 25. The horn 22 is supported so as to be capable of oscillation in an axial direction indicated by an arrow 20, and a blade 30 is secured to the terminal end of the end portion 28 by means of a set screw 37 so as to extend in a direction perpendicular to the axial direction of the horn 22. The blade 30 is in the form of an elongate plate having a pair of edge members 30a, 30b of similar configuration and which are disposed on the opposite sides of the longitudinal center. The screw 37 mounts the blade 30 on the end 28 of the horn at the longitudinal center and in a replaceable manner. The blade 30 has a length which corresponds to one wavelength of the resonant frequency of the blade 30 which in turn depends on the natural frequency of the ultrasonic vibrator 23, or slightly greater. Accordingly, each edge member 30a, 30b has one-half such length. The width and the thickness of the blade 30 may be chosen as described above in connection with the embodiment of FIG. 2. When the ultrasonic vibrator 23 is excited, each edge member 30a or 30b of the blade 30 undergoes a bending motion in a direction indicated by a double-headed arrow 32. In use, the end of a selected one of edge members, 30a, is brought into contact with the pericementum 102 located between the tooth 100 and the alveolar bone 101 while slowlying moving the blade 30 in a direction indicated by an arrow 33. This permits the pericementum 102 to be cut with a greatly reduced cutting resistance while spacing the tooth 100 and the alveolar bone 101 apart and while the pain transmitting system of the tooth 100 is insensitized by the ultrasonic oscillation thereof.

FIG. 4 shows an auxiliary exciting tool 300 which is preferred for use with the tooth extracting tool 200 shown in FIG. 2. It will be apparent from the foregoing description that when the tooth 100 is subjected to ultrasonic oscillation transmitted from the blade 19 of the tool 200, the pain transmitting system of the tooth 100 is insensitized, and a patient experiences little pain if the pericementum 102 which supports the tooth 100 is cut by the blade 19. The insensitization of the pain transmitting system is assured by maintaining the ultrasonic oscillation of the tooth 100, but as the cutting resistance increases during the time the pericementum 102 is being cut, the ultrasonic oscillation may cease though termporarily. To cope with this possibility, the use of the auxiliary exciting tool 300 which assists in maintaining the excitation of the tooth 100 by the blade 19 may be contemplated.

The auxillary exciting tool 300 includes a hand-held grip 34, similar to that of the tooth extracting tool 200, and an ultrasonic vibrator 35 is housed within the grip 34. The vibrator 35 is operatively connected to a horn 36, which is in turn connected to a rod-shaped applicator 37 which projects through an opening formed in a the grip 34. The applicator 37 is carried together with the horn 36 in known manner by the grip 34 so as to be capable of axial oscillation in a direction indicated by a double-headed arrow 38 as the vibrator 35 oscillates.

The exciting tool 300 is held by hand and urged against the tooth in a direction indicated by an arrow 39 so that the end of the applicator 37 is maintained in contact with an affected tooth 100 under a given pressure. As a consequence, the tooth 100 is subjected to ultrasonic oscillation from the exciting tool 300, in addition to ultrasonic oscillation transmitted from the blade 19 of the tooth extracting tool 200, thereby assuring that the ultrasonic oscillation of the tooth 100 is maintained by means of the tool 300 if the transmission of the ultrasonic oscillation from the blade 19 is interrupted as a result of overload thereof. The vibrator 35 of the tool 300 may be connected to a source, not shown, of the same high frequency as that to which the vibrator 23 of the tool 200 is connected. The frequency and the amplitude of oscillation of the vibrator 35 may be chosen equal to those of the vibrator 23 or may be different therefrom. The use of the auxiliary exciting tool 300 assures the insensitization of the pain transmitting system and also improves the cutting efficiency of the pericementum 102 by the blade 19 of the tooth extracting tool 200. While a theoretical explanation for the improvement in the cutting efficiency of the blade 19 cannot be given at this stage, a remarkable effect is experienced in actual operations.

FIG. 5 shows a tooth extracting tool according to another embodiment of the invention. Same reference characters are used as used previously to designate corresponding parts. It is to be noted that the blade 19 of the tool 200 shown in FIG. 2 is subjected to ultrasonic oscillation of a reduced amplitude which is transmitted from the ultrasonic vibrator 23, but a blade 19 used in this embodiment is additionally subjected to a low frequency oscillation of an increased amplitude separately. Specifically, a tooth extracting tool 400 includes an internal housing 40 which houses an ultrasonic vibrator 23 together with its associated horn 22. A bearing sleeve 43 is securely mounted on the outside of the housing 40, and is formed with a pair of outwardly extending flanges 43a at its opposite ends. The internal housing 40 is slidably fitted into a hand-held grip 41, serving as an external housing, with the bearing sleeve 43 interposed therebetween. To assure a smooth sliding movement of the internal housing 40, a ball bushing 42 is interposed between the internal wall of the grip 41 and the bearing sleeve 43 secured around the internal housing 40. At its one end, the grip 41 is formed with an opening 50 having a diameter greater than the diameter of the internal housing 40, with the edge of the opening 50 being defined by a radially inward lip 41b. At its other end, the grip 41 is internally formed with a shoulder 41a. Disposed within the grip 41 are a first coiled spring 44 located between the shoulder 41a and one of flanges 43a of the bearing sleeve 43 and a second coiled spring 45 located between the lip 41b of the grip 41 and the other flange 43a of the bearing sleeve 43. The first and the second coiled spring 44, 45 are disposed in surrounding relationship with the internal housing 40, maintaining it at its neutral position. A drive shaft 47 extends through the grip 41 and has an eccentric cam 48 mounted thereon, which is disposed in engagement with a plate-shaped cam follower 46 which is secured to the rear end of the internal housing 40. While not shown, the drive shaft 47 may be connected to a miniature motor or an air turbine disposed within the grip 41 or may be operatively connected to a drive source, which is separate from the grip 41, through a flexible elongate rotatable shaft of conventional construction.

The internal housing 40 receives the ultrasonic vibrator 23 including a horn 22 therein, which are constructed in a similar manner as in the tool shown in FIG. 2. The horn 22 extends through an opening formed in the internal housing 40, and its externally projecting end carries a blade 19 in a replaceable manner.

The ultrasonic vibrator 23 located within the internal housing 40 excites the blade 19 in the axial direction of the horn 22, as indicated by an arrow 55, through the horn, while the eccentric cam 48 located within the grip 41, corresponding to the external housing, excites the internal housing 40 in the same direction as the blade 19 is excited, as indicated by an arrow 56, as the cam 48 rotates in a direction indicated by an arrow 49. The excitation by the ultrasonic vibrator 23 may take place at a frequency of 20 to 80 kHz and with an amplitude of 4 to 15 micrometers while the excitation of the internal housing 40 by means of the eccentric cam 48 may preferably take place at a secondary frequency of 100 Hz and with an amplitude of 0.3 mm. In use, the grip 41 of the tool 400 is held by hand as described above, and the tool 400 is slowly moved in a direction indicated by an arrow 57 so that the blade 19 cuts through the pericementum 102 located between the tooth 100 and the alveolar bone 101. In distinction to the embodiment mentioned above, the ultrasonic oscillation of a reduced amplitude produced by the ultrasonic vibrator 23 and a low frequency oscillation of an increased amplitude produced by the eccentric cam 48 are superimposed as they are applied to the blade 19, thereby greatly increasing the cutting rate of the pericementum. However, it should be noted that the low frequency oscillation of an increased amplitude causes a significant displacement to a spring associated with the pericementum, disadvantageously causing a patient to experience pains, though diminished in degree, as compared with the cutting performed with the ultrasonic oscillation of a reduced amplitude alone. However, such technique is still effective to achieve a medical operation within a reduced length of time with pain suppressed at permissible levels.

We claim;

1. A dental tool for extracting a tooth which is secured to an alveolar bone through a pericementum, comprising a cylindrical housing, an acoustic transducer disposed within the housing and opertive to be driven from a source of a high frequency power which is arranged externally of the housing for producing vibrational energy of a predetermined frequency and a predetermined amplitude, a vibrating member having one end thereof connected to the acoustic transducer, and a blade attached to the other end of the vibrating member in a replaceable manner, the blade having an edge which is disposed externally of the housing and having a thickness which is substantially less than the thickness of the pericementum, the acoustic transducer having an oscillating frequency higher than the natural frequency of the tooth, the acoustic transducer exciting the blade through the vibrating member so that an amplitude of oscillation as measured at the edge of the blade is equal to or less than 15 micrometers.

2. A dental tool according to claim 1 in which the blade comprises a flat elongate plate and has the edge formed at one longitudinal end while the other longitudinal end thereof is attached to the vibrating member in a replaceable manner, whereby it is longitudinally excited by the acoustic transducer through the vibrating member.

3. A dental tool according to claim 1 in which the blade comprises a flat, elongate plate having edges at its longitudinal ends, the blade being mounted, intermediate its length, to the other end of the vibrating member to be perpendicular thereto and in a replaceable manner, whereby the blade is excited in a direction perpendicular to the length thereof from the acoustic transducer through the vibrating member.

4. A dental tool according to claim 1, further comprising another acoustic transducer driven from the source of high frequency power, another vibrating member connected to said another acoustic transducer, and an applicator connected to said another vibrating member, the applicator causing an ultrasonic oscillation of the tooth as the blade cuts through the pericementum.

5. A dental tool according to claim 1, further comprising an external housing, bearing means for supporting the first mentioned housing in an axially slidable manner within the external housing, spring means interposed between the first mentioned housing and the external housing for maintaining the first mentioned housing at its neutral position within the external housing, and a vibration generator for exciting the first mentioned housing in the axial direction thereof about the neutral position.

6. A dental tool according to claim 5 in which the vibration generator has a frequency less than the natural frequency of the tooth and has an amplitude greater than the amplitude of the blade as it is driven by the first mentioned transducer.

* * * * *